United States Patent
Limaye et al.

(10) Patent No.: US 10,821,237 B2
(45) Date of Patent: Nov. 3, 2020

(54) PEN NEEDLE

(71) Applicant: Becton, Dickinson and Company, Franklin Lakes, NJ (US)

(72) Inventors: Amit Limaye, Wayne, NJ (US); Sudarsan Srinivasan, North Brunswick, NJ (US); David Schiff, Highland Park, NJ (US); Todd Sack, Dover, DE (US); Breanna Stachowski, Philadelphia, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 115 days.

(21) Appl. No.: 15/989,465

(22) Filed: May 25, 2018

(65) Prior Publication Data

US 2018/0339115 A1 Nov. 29, 2018

Related U.S. Application Data

(60) Provisional application No. 62/511,610, filed on May 26, 2017.

(51) Int. Cl.
*A61M 5/32* (2006.01)
*A61M 5/00* (2006.01)
*A61M 5/50* (2006.01)

(52) U.S. Cl.
CPC .......... *A61M 5/3234* (2013.01); *A61M 5/002* (2013.01); *A61M 5/3202* (2013.01);
(Continued)

(58) Field of Classification Search
CPC .............. A61M 5/3243; A61M 5/3202; A61M 5/3213; A61M 5/3271; A61M 5/32;
(Continued)

(56) References Cited

U.S. PATENT DOCUMENTS 6,986,760 B2  1/2006  Giambattista et al.
7,314,464 B2  1/2008  Giambattista et al.
(Continued)

FOREIGN PATENT DOCUMENTS

CN    104491955 A    4/2015
WO    WO-2015085031 A1 *  6/2015  ............ A61M 5/002

OTHER PUBLICATIONS

European Search Report dated Aug. 24, 2018, which issued in corresponding European Patent Application No. 18173874.1.

*Primary Examiner* — Nathan R Price
*Assistant Examiner* — Anna E Goldberg-Richmeier
(74) *Attorney, Agent, or Firm* — Dickinson Wright PLLC

(57) ABSTRACT

A pen needle assembly (10) includes a pen needle (12) with a hub body (16) having a needle shield (28) that covers a needle (26) and can be retracted to expose the needle during injection and return to the extended position after use and locked in the extended position. A spring (56) is provided to rotate the needle shield after use to a locked position. A locking member (84) can be provided on the needle shield that cooperates with the hub body (16) to prevent rotation after use. An attachment mechanism (38) for the pen needle provides a sensory indication when a needle-bearing hub body (16) is seated on a pen and limits further rotation of the pen needle relative to the delivery device.

30 Claims, 16 Drawing Sheets

(52) U.S. Cl.
CPC ........ *A61M 5/3213* (2013.01); *A61M 5/3271* (2013.01); *A61M 5/3272* (2013.01); *A61M 5/3293* (2013.01); *A61M 5/50* (2013.01); *A61M 2005/3228* (2013.01); *A61M 2005/3247* (2013.01); *A61M 2005/3254* (2013.01); *A61M 2005/3267* (2013.01); *A61M 2205/581* (2013.01); *A61M 2205/582* (2013.01); *A61M 2205/583* (2013.01)

(58) Field of Classification Search
CPC .... A61M 2005/3228; A61M 2205/583; A61M 2005/3247; A61M 5/3273; A61M 5/3293
See application file for complete search history.

(56) References Cited

U.S. PATENT DOCUMENTS

| | | | |
|---|---|---|---|
| 7,462,168 B2 | 12/2008 | Stonehouse et al. | |
| 7,462,169 B2 | 12/2008 | Follman et al. | |
| 7,540,858 B2 | 6/2009 | DiBiasi | |
| 7,666,164 B2 | 2/2010 | Giambattista et al. | |
| 8,632,503 B2 | 1/2014 | Ruan et al. | |
| 8,827,956 B2 | 9/2014 | Banik et al. | |
| 8,858,498 B2 | 10/2014 | West | |
| 9,162,030 B2 | 10/2015 | Ruan et al. | |
| 9,352,102 B1 | 5/2016 | Quinn et al. | |
| 9,457,157 B2 | 10/2016 | Carrel et al. | |
| 9,623,194 B2 * | 4/2017 | Srinivasan | A61M 5/3202 |
| 9,642,971 B2 | 5/2017 | Newman et al. | |
| 10,022,505 B2 | 7/2018 | Hu | |
| 10,322,250 B2 | 6/2019 | Newman et al. | |
| 10,398,858 B2 | 9/2019 | Newman et al. | |
| 10,420,900 B2 | 9/2019 | Carrel et al. | |
| 2002/0004648 A1 | 1/2002 | Larsen et al. | |
| 2011/0257603 A1 | 10/2011 | Ruan et al. | |
| 2015/0157808 A1 | 6/2015 | Srinivasan et al. | |
| 2016/0144129 A1 * | 5/2016 | Mosebach | A61M 5/31585 604/193 |
| 2017/0021110 A1 | 1/2017 | Srinivasan et al. | |
| 2019/0125978 A1 * | 5/2019 | Daily | A61M 5/326 |

* cited by examiner

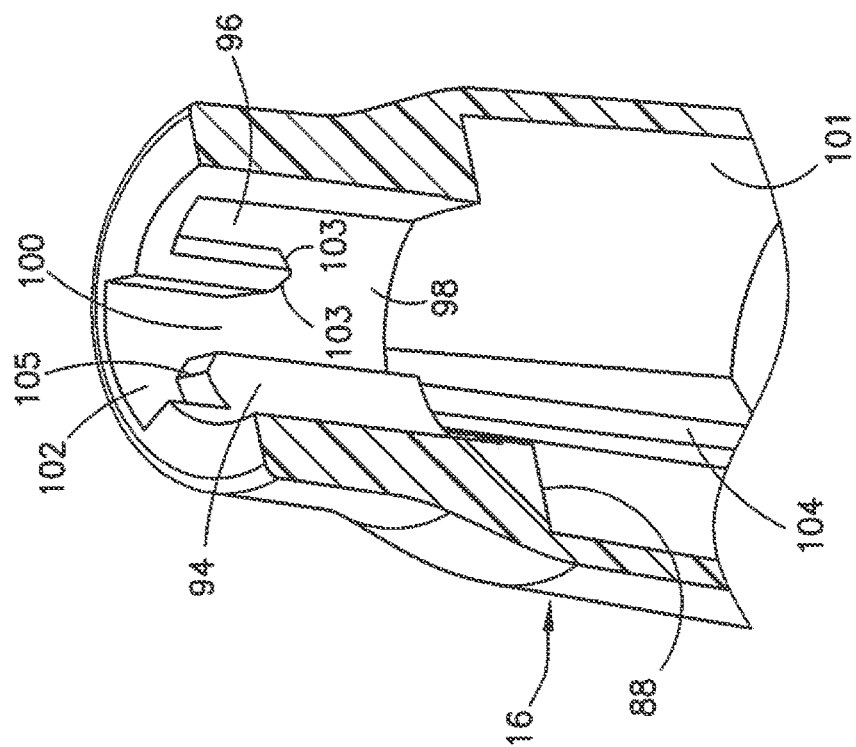
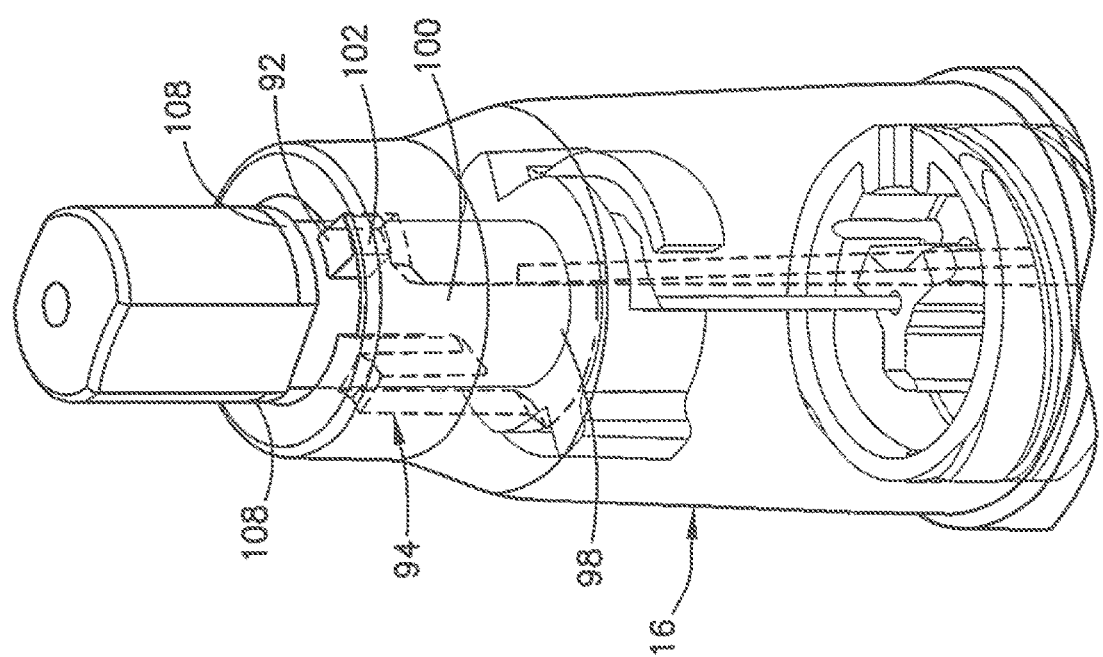

PEN NEEDLE

This application claims priority to U.S. Provisional Patent Application Ser. No. 62/511,610 filed on May 26, 2017, which is hereby incorporated by reference in its entirety.

BACKGROUND OF THE INVENTION

Field of the Invention

The invention is directed to a pen needle adapted for attachment to a medication delivery device such as a medication delivery pen. The pen needle assembly according to the invention has a pen needle with a retractable needle shield where the needle shield can be retracted during use and extended to a locked position after use to cover the needle. A cover includes a sensory feedback, such as an audible clicking sound or tactile sensation to indicate the pen needle is fully seated on the delivery pen and a stop member to prevent overtightening.

Description of the Related Art

Pen needles are used to attach to a medication pen and are especially useful for delivering self-administered injectable medications such as insulin. In one known commercial device, a needle-bearing hub is provided inside a funnel-shaped outer cover, sometimes referred to as the "outer shield," or simply as the "cover." The cannula is affixed in an axial bore of the hub with one end protruding from the distal or "patient side" of the hub and the other end of the needle is recessed in a cavity on the proximal or "non-patient" side of the hub, adapted for attachment to the medication pen. A paper and foil "teardrop" label is heat sealed on the edge of the open end of the funnel shaped outer cover. In addition, the medication pen may have a cap received over the distal end of the medication pen, over the opening where the pen needle is installed. To install the pen needle on a medication pen, the user removes the medication pen cap. The user then removes the label on the pen needle outer cover and holds the outer cover to install the hub, typically threading the hub onto the pen. Once the hub is installed on the medication pen, the outer cover can be removed by pulling the outer cover distally off the hub. A separate inner needle shield sits over the needle, which the user must remove to administer an injection. The inner shield generally sits on the hub and simply helps the user locate the needle without forming a sterility barrier. After use, the user may use the outer cover to unthread the hub from the pen and dispose of the pen needle.

Medication pens and associated pen needles are disclosed in U.S. Pat. No. 7,645,264, and U.S. Patent Application Publication Nos. 2009/0069755 and 2012/0022460, all of which are incorporated by reference in their entirety for their teaching of pen needle design and construction. A device for arranging a releasable pen needle on an injection pen and releasing the pen needle into a mating storage or disposal container is disclosed in U.S. Pat. No. 8,057,444, also incorporated by reference.

With the prior art described above, it is not always possible for the user to tell that the hub is properly seated on the medication pen. The pen does not provide a sensory feedback that the pen needle is seated on the pen (other than the tightening of the threaded connection itself). This can lead to over-tightening the pen needle on the pen, which would render the pen needle difficult to remove, or under-tightening the pen needle on the pen, which could cause the pen needle to leak. Likewise, when removing the needle, the outer cover does not always align properly over the hub and it may take two or more tries to unscrew the hub. Although passively shielded pens are known, including pen needles which shield the non-patient end of the needle automatically after use, many pen needles simply leave the non-patient end of the needle exposed after use, relying on the proximal end cavity to provide protection from accidental needle sticks after use.

While the prior devices are generally suitable for the intended use, there is a need in the industry for improvements to the pen needles.

SUMMARY

The invention is directed to a pen needle with a retractable needle shield where the needle shield can lock in an extended position to cover the end of the needle after use.

One feature of the invention is to provide sensory feedback when a pen needle is seated securely on a delivery device, such as a medication pen or delivery pen. Sensory feedback includes an audible and/or tactile sensation indicating correct attachment to the delivery device. A stop member is included to stop rotation of the pen needle after properly seated on the delivery pen. An advantage of the pen needle is to use less plastic material in the pen needle construction and to provide features to enhance ease of use.

The pen needle is able to attach to a delivery pen or other delivery device where the pen needle includes a needle shield that can lock in place after use to cover the exposed end of the needle. The pen needle of the invention can include a needle shield that is in an extended position before use and can retract to expose a needle or cannula during use, and then can be deployed after use to cover the needle or cannula.

The pen needle in one embodiment includes a hub body supporting a needle. A cover can be fitted over the end of the hub body to cover the needle during storage until ready for use. The hub body supports a needle retainer that supports the needle. A movable needle shield is mounted to the hub body that can retract during use to expose the needle and can be deployed by moving or sliding outwardly after use to cover the end of the needle and prevent further use or accidental needle stick. A biasing member, such as a spring member is provided between the needle shield and the retainer to bias the needle shield outwardly.

In one embodiment, the spring member is positioned within the hub body for biasing the needle shield outwardly to the extended position covering the distal end of the needle. The spring member can also provide a torsional force to the needle shield to rotate the needle shield to a locked position preventing re-use of the device.

In one embodiment, the cover and pen needle are configured to provide a mechanism that provides an audible sound and/or a tactile feel to indicate to the user when the hub body is properly attached to the delivery pen. A rib or other detent can be provided on the inner surface of the cover that slides over a flexible tab on the hub body to provide the audible sound. The tab can be formed on a flexible or resilient portion on the outer surface of the hub body or can be a flexible member. A stop member can be provided on the outer surface of the hub body and spaced from the tab to prevent further rotational movement of the cover relative to the hub body and provide a tactile and/or audible indication that the hub body is in the proper position on the delivery pen.

The features of the invention can be attained by providing a needle shield that can be retracted during use to expose the needle and can be deployed to cover the needle where the needle shield has a tab that slides in a track in the hub body. The needle shield and the tab slide and rotate to lock the needle shield in the extended position by rotating the tab to the locked position within the track. In one embodiment, the needle shield can be rotated by a spring member that biases the needle shield to the extended position. The spring member can provide a biasing force to extend the shield over the needle and apply a torsional force to rotate the needle shield where the tab slides to a locked position in the track.

The needle shield in one embodiment can include one or more flexible tabs that project radially outward and engage an inner surface of the hub body. During use the needle shield can rotate when in the extended position where the tabs slide over a stop member thereby retaining the needle shield in a locked position and preventing further rotation. The tabs can engage a rib or recess on the inner surface of the hub body to prevent the needle shield from rotating back to the original position so that the needle shield cannot retract into the hub body. The needle shield can include one or more outwardly extending tabs that are able to slide in a track formed on the inner surface of the hub body to allow the needle shield to slide axially between the extended position and the retracted position and allow the needle shield to rotate to the locked position.

The features of the invention can also be attained by providing a spring to actuate the needle shield by applying a torsional force to rotate the needle shield and a biasing force to deploy the needle shield.

The features of the invention are attained by providing a pen needle comprising a hub body having a proximal end for attachment to a delivery device and a distal end. A needle is coupled to the hub body and having a distal end extending from said distal end of the hub body. A needle shield is mounted in the hub body for sliding between an extended position to cover the needle and a retracted position to expose the distal end of the needle. The needle shield is rotatable from a first angular position where the needle shield slides in the hub body to a second angular position where the needle shield is locked in the extended position.

The features of the invention are also attained by providing a pen needle where the needle shield includes at least one tab that slides within a track to allow the needle shield to slide between the extended position and the retracted position and to rotate from the first angular position to the second angular position.

The features of the invention are further attained by providing a pen needle where a track in the hub body includes a first longitudinal section that allows the needle shield to slide from a first extended position to the retracted position and a second longitudinal section that allows the needle shield to slide from the retracted position to a second extended position.

A pen needle includes a hub body having a proximal end for attachment to a delivery device and a distal end. A needle is coupled to the hub body and has a distal end extending from the distal end of the hub body. A needle shield is mounted in said hub body for sliding in the hub body. The needle shield has at least one radially extending tab that slides within a track formed on an inner surface of the hub body for sliding the needle shield between a first extended position to cover the needle, a retracted position to expose the distal end of the needle, and a second extended position to cover the distal end of the needle. The needle shield is rotatable from a first angular position where the needle shield slides in the track of the hub body from the first extended position to the retracted position to a second angular position where the needle shield slides to the second extended position where the needle shield is locked in the second extended position.

A method of using the pen needle, such as for injecting a substance into a patient, is also provided. The method retracts the needle shield from a first extended position to a retracted position to expose the needle. The needle shield is then rotated from a first angular position to a second angular position by a biasing member such as a spring. The needle shield is then moved to a second extended position to cover the needle and rotated to an angular position with respect to the hub body to lock the needle shield in the extended position.

A method a attaching the pen needle to a delivery device is provided by threading the threaded end of the hub body to the end of a delivery device. An outer cover on the hub body is rotated until the hub body is seated on the delivery device. A rib on an inner surface of the cover slides over a tab on an outer surface of the hub body to provide an audible or tactile sensation to prevent over tightening of the hub body on the delivery device. The tab on the hub body can be formed on a flexible portion of the wall of the hub body or can a flexible tab or member that is able to cooperate with the rib on the cover.

These and other aspects and features of the invention will be apparent from the following detailed description of the invention and the drawings.

BRIEF DESCRIPTION OF THE DRAWINGS

The following is a brief description of the drawings, in which:

FIGS. 14A-14E show the sequential movement of the mechanism for the needle shield during use;

FIG. 15 is a cross sectional view of the hub body showing the track; and

The figures are not to scale, and some features are omitted in certain views to better illustrate other features.

DETAILED DESCRIPTION

As used herein, the "distal" direction is in the direction of the injection site, and the "proximal direction" is the opposite direction. The "axial" direction is along the longitudinal axis of the injection device. The needle cannula is generally arranged axially in the device. "Radially" is a direction perpendicular to the axial direction. Thus, "radially inward" generally means closer to the needle. "Circumferentially" means arranged around the circumference, so that threads are arranged circumferentially on the end of a threaded fitting. The "top" view of a pen needle is looking at the pointed end of the needle. The different features of the embodiments can be used in combination with and used with other embodiments as long as the combined parts are not inconsistent with or interfere with the operation of the device and assembly.

Figure 4:
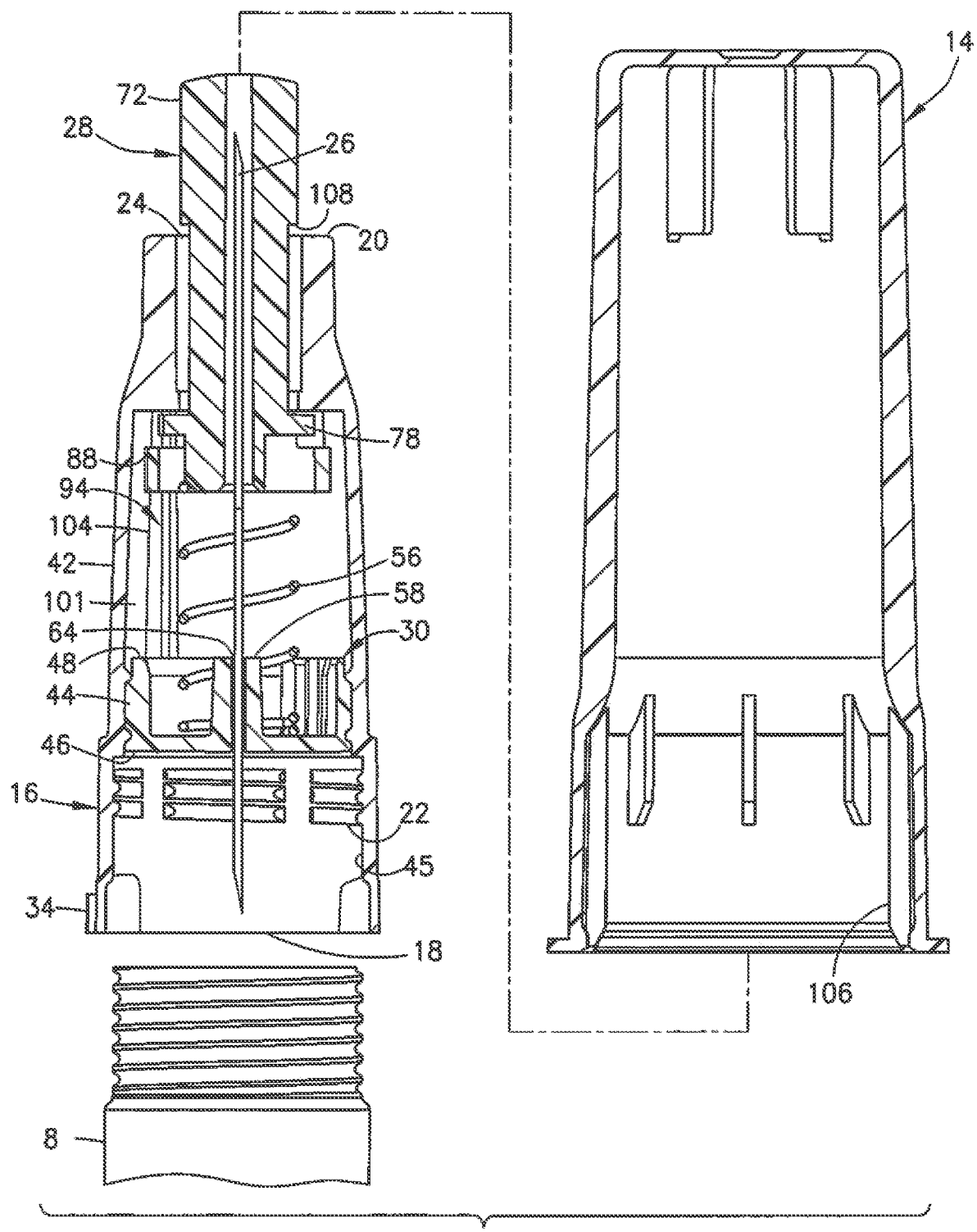
FIG. 4 is cross sectional side view of the cover and hub body of the pen needle.

Referring to the drawings, the pen needle assembly 10 of the invention includes a pen needle 12 and a cover 14 that fits over the pen needle 12. The cover 14 encloses the pen needle 12 during storage and assists in attaching the pen needle 12 to a delivery pen. A closure or peel tab is generally provided over the open end of the cover to maintain the needle hub assembly in a sterile condition until ready for use. The delivery pen 8 is shown in FIG. 4. It will be understood that the delivery pen can be a typical delivery pen or other medication delivery device as known in the art for dispensing and delivering a medication or pharmaceutical such as insulin. An example of a suitable delivery pen is disclosed in U.S. Pat. No. 9,774,844, which is hereby incorporated by reference.

In the embodiment shown in FIGS. 1-4, the pen needle 12 includes the hub body 16, a needle shield 28, a biasing member shown as a spring 56, and a needle retainer 30 coupled to the hub body 16. The hub body 16 includes an open bottom end 18 defining a proximal end and a top end 20 defining a distal end. The hub body 16 in the embodiment shown in FIGS. 2 and 4 has a substantially conical shaped top portion that tapers toward the top end face 20. The open bottom end 18 is provided with internal threads 22 shown in FIG. 4 for coupling to the delivery pen in a known manner. The top end 20 defines an opening 24 for the needle 26 or cannula and defines the skin contact surface during use. Needle 26 can be a hollow steel needle with a sharpened tip having a gauge and length for penetrating the skin to a desired depth.

Figure 1:
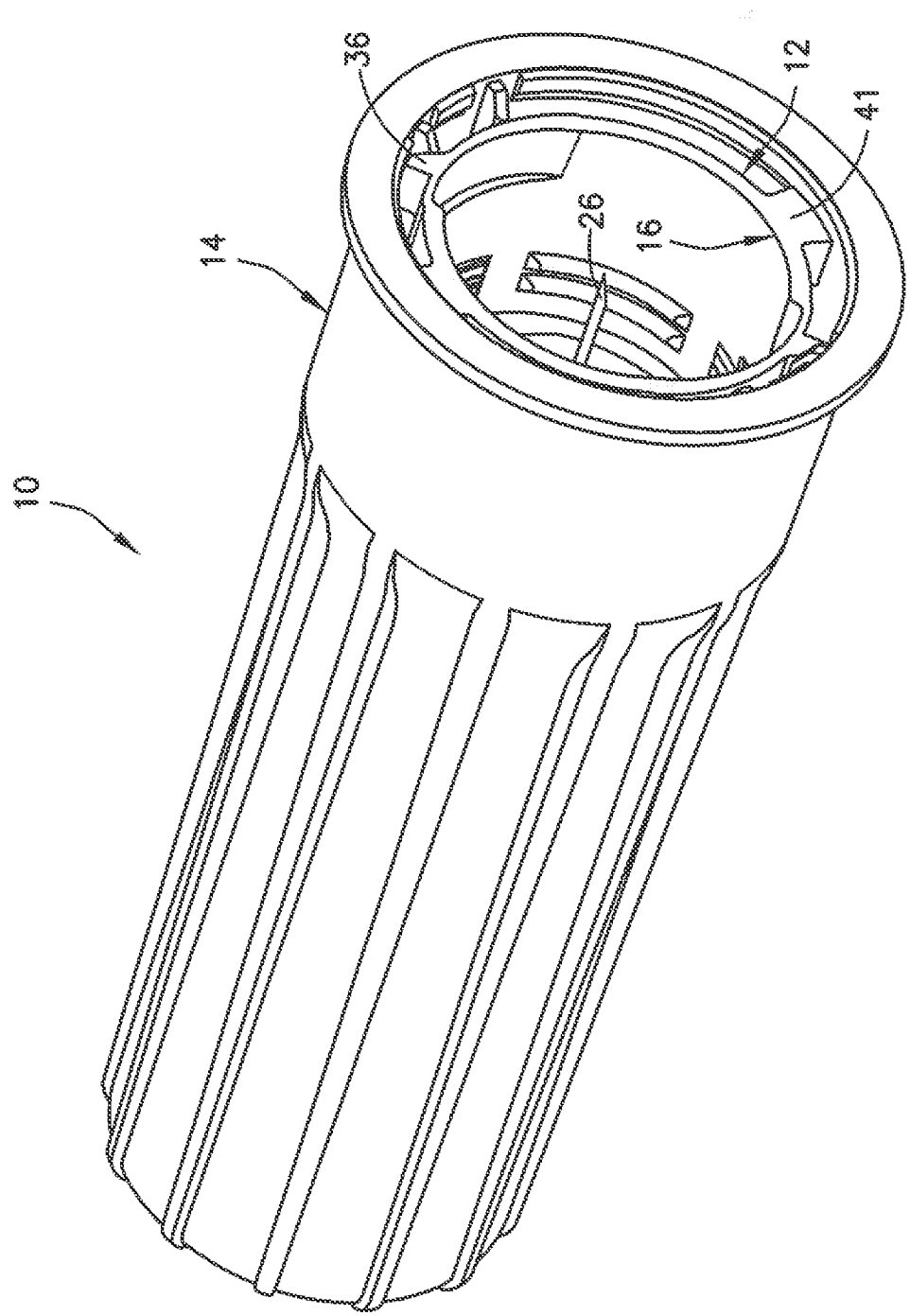
FIG. 1 is a perspective view of a pen needle with an outer cover according to one embodiment of the pen needle.
Figure 2:
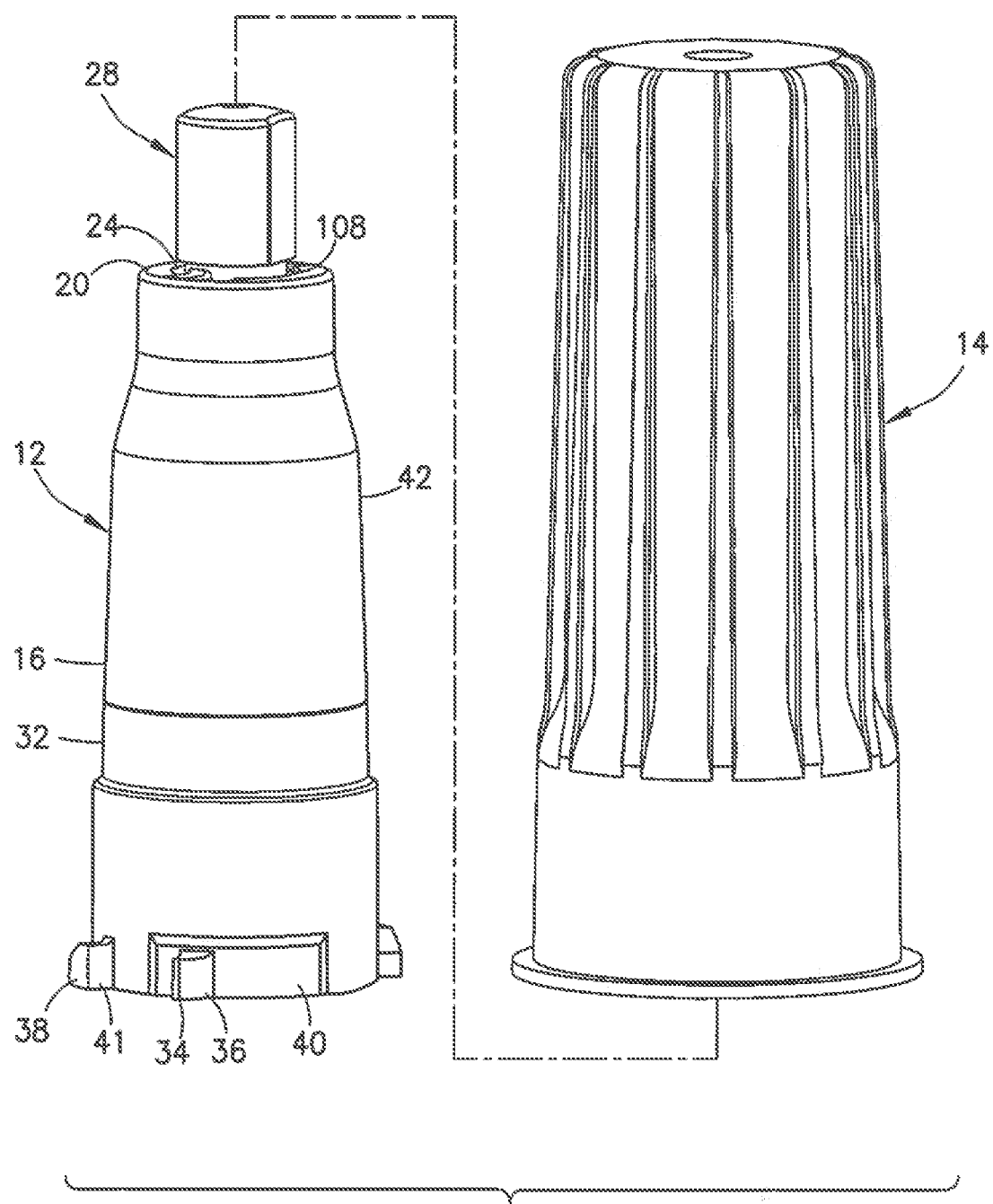
FIG. 2 is an exploded side view showing the outer cover and hub body of the pen needle.
Figure 3:
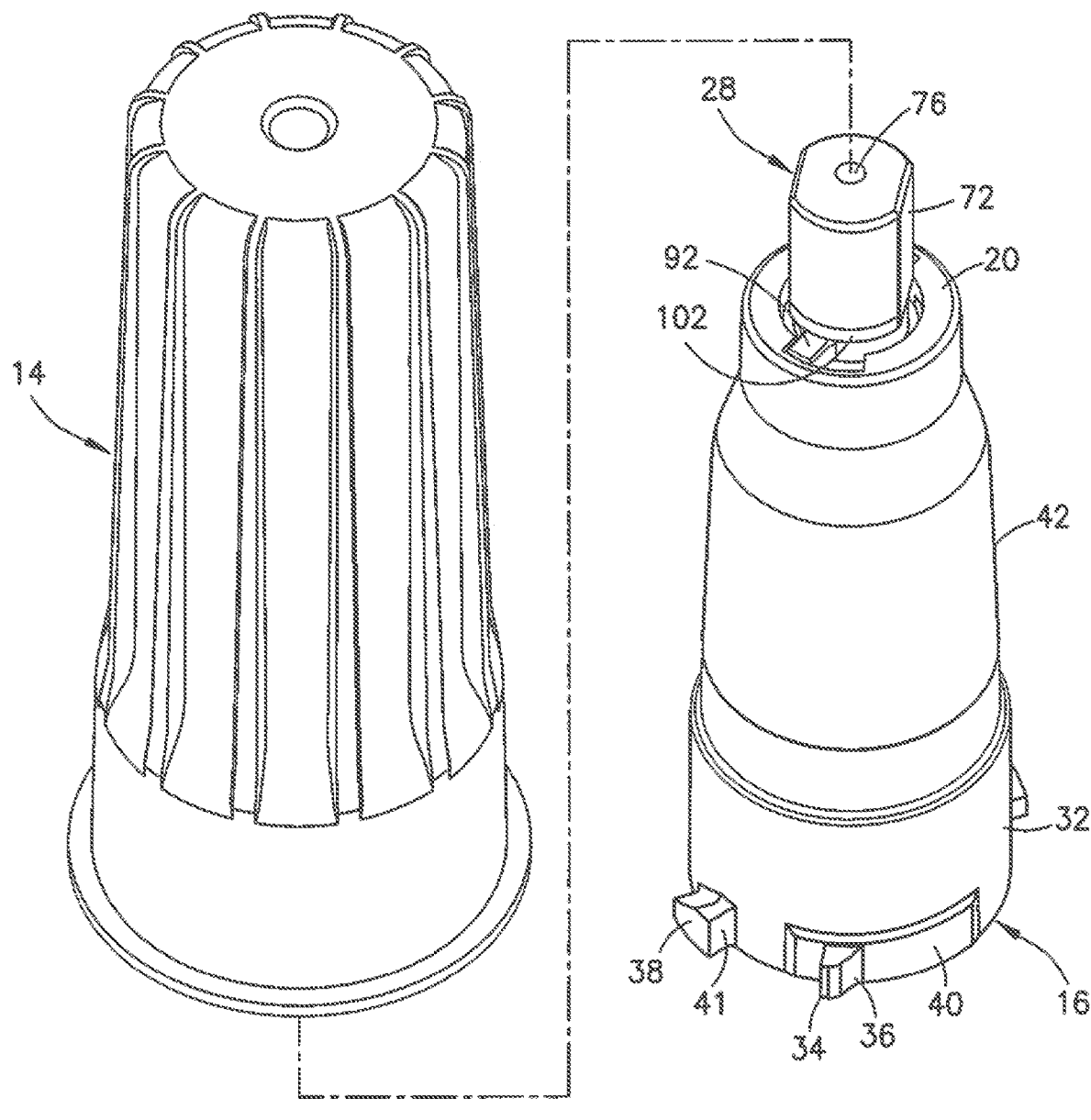
FIG. 3 is an exploded perspective view showing the outer cover and hub body of the pen needle.
Figure 5:
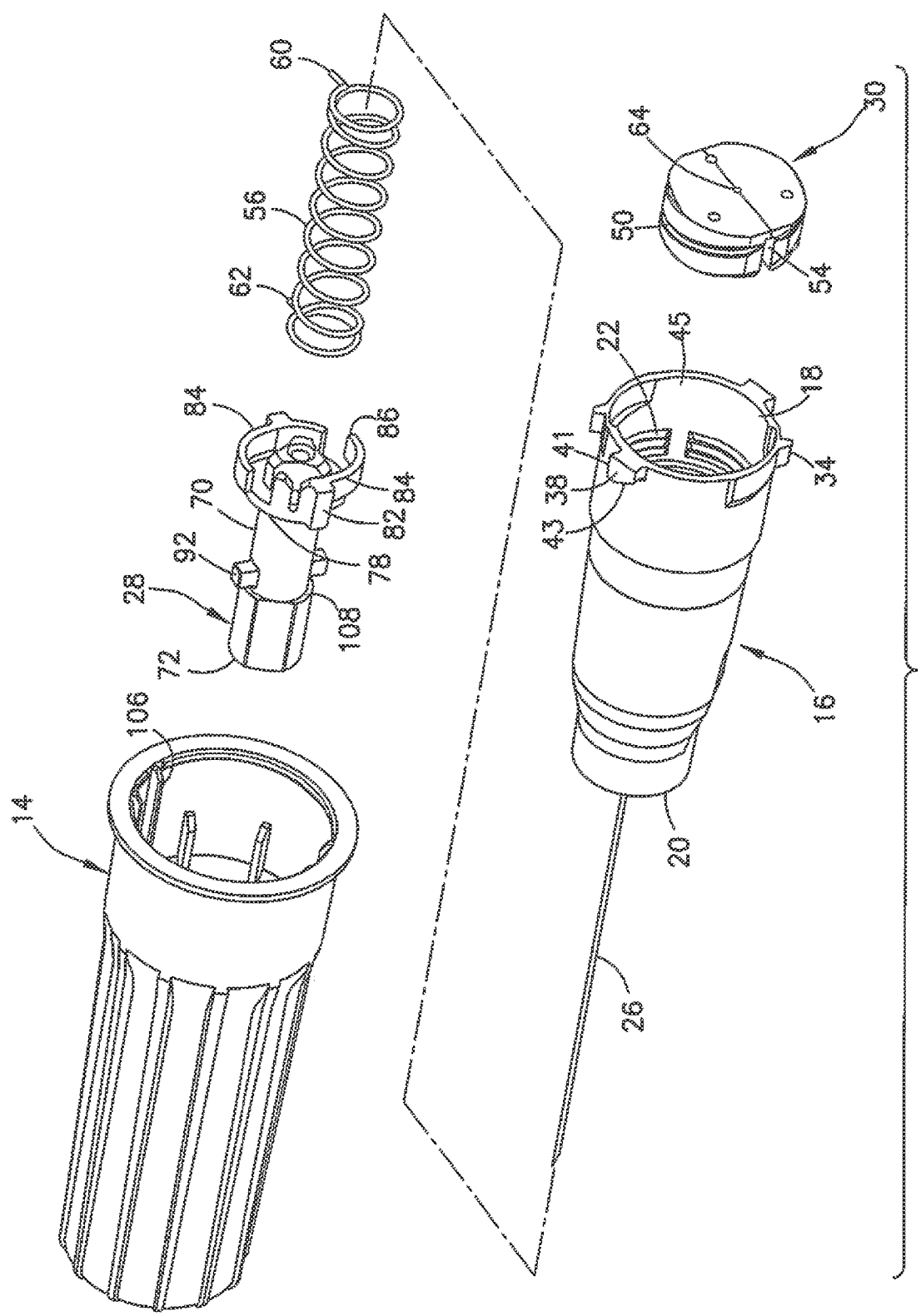
FIG. 5 is an exploded view of the pen needle.

The hub body 16 has a bottom end with a substantially cylindrical outer surface 32. A tab 34 projects radially outward from the outer surface 32 at the open bottom end 18 as shown in FIG. 5. The tab 34 has an inclined face 36 facing outward for cooperating with the cover 14 as discussed herein. As shown in FIGS. 2 and 3, the tab 34 is formed on a flexible member 40 that is formed with the hub body 16 so that the tab 34 and the flexible member 40 can deflect inwardly or downwardly when the cover engages the tab 34. The flexible member 40 is formed as a flexible portion or section of the wall and has a thinner thickness so as to allow the section forming the flexible member 40 to deflect inwardly when contacted by a rib 106 on the cover. In other embodiments, the flexible member 40 can be formed as flexible finger or tab that can deflect inwardly or upwardly when engaged with the cover.

Figure 6:
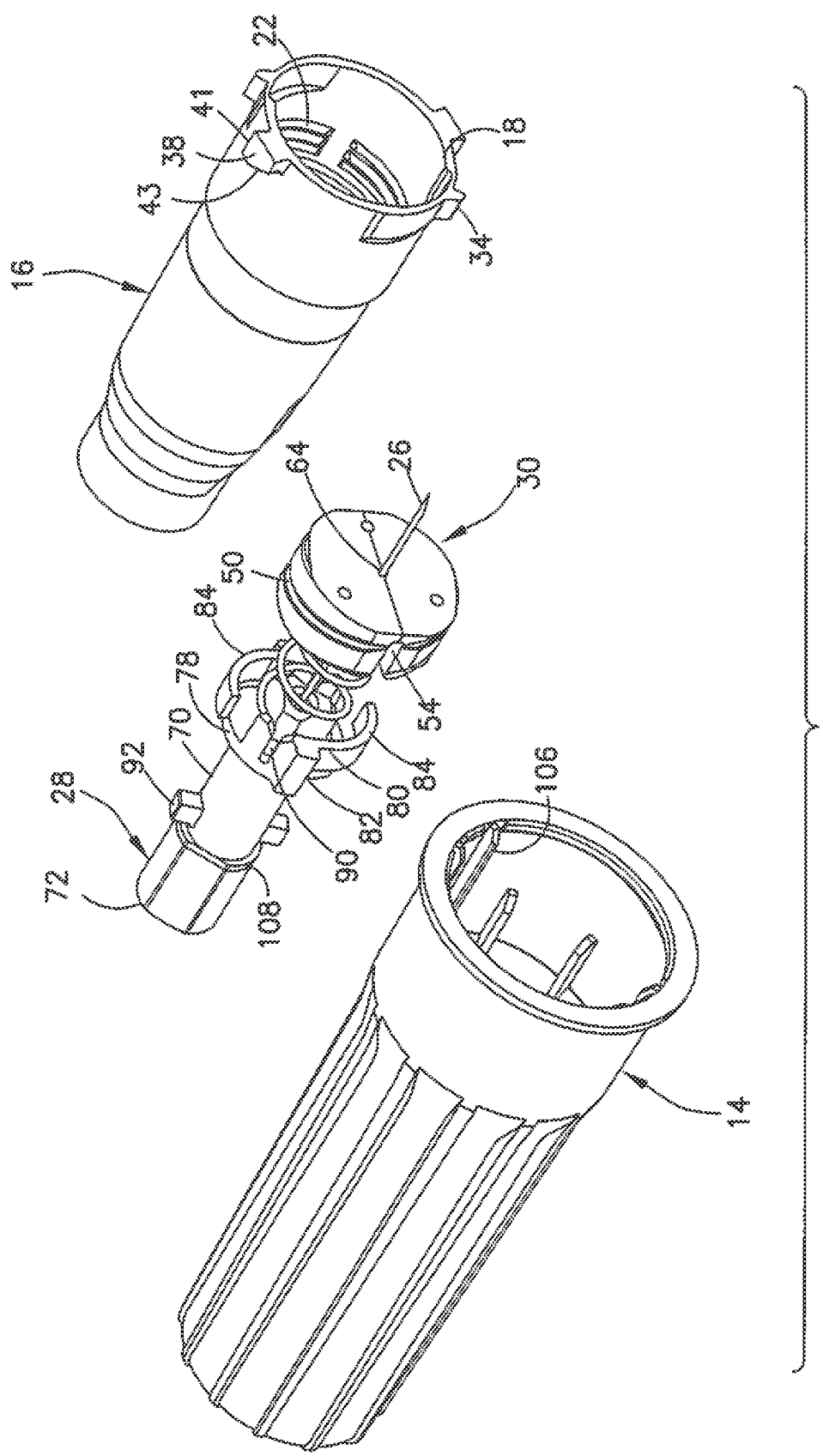
FIG. 6 is an exploded view of the pen needle showing the needle shield assembly.

A lug 38 is also formed on the outer surface 32 of the body 16 at the open bottom end 18 and spaced circumferentially from the tab 34. The lug 38 in the embodiment shown in FIG. 2 and FIG. 6 has a flat leading face 41 oriented substantially perpendicular to the longitudinal axis of the hub body 16. An inclined face 43 faces toward the top distal end of the hub body 16 as shown in FIGS. 2 and 6. In the embodiment shown, two tabs 34 and two lugs 38 are spaced around the perimeter of the open bottom end 18 on opposite side of the hub body as shown FIG. 6.

Figure 10:
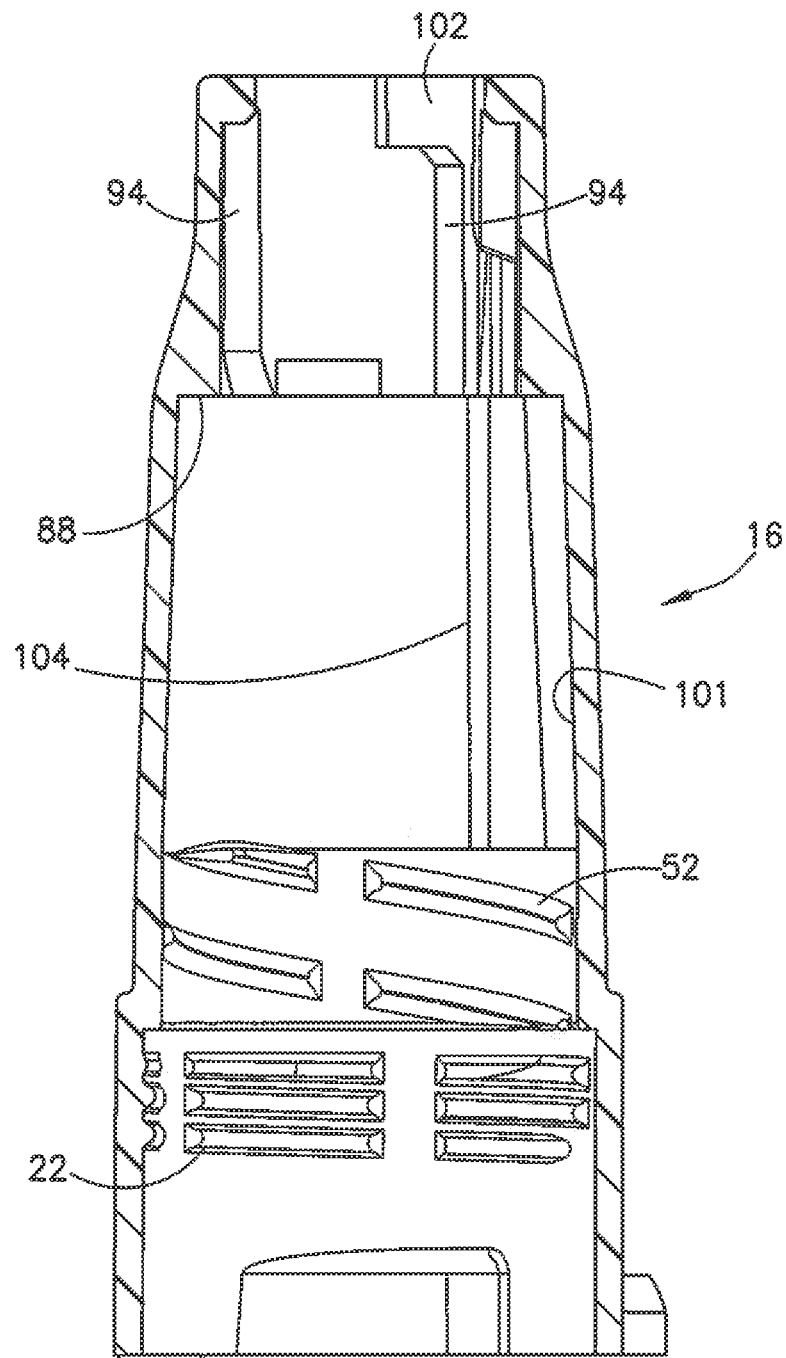
FIG. 10 is a cross sectional side view of the hub body of the pen needle without the needle shield.
Figure 16:
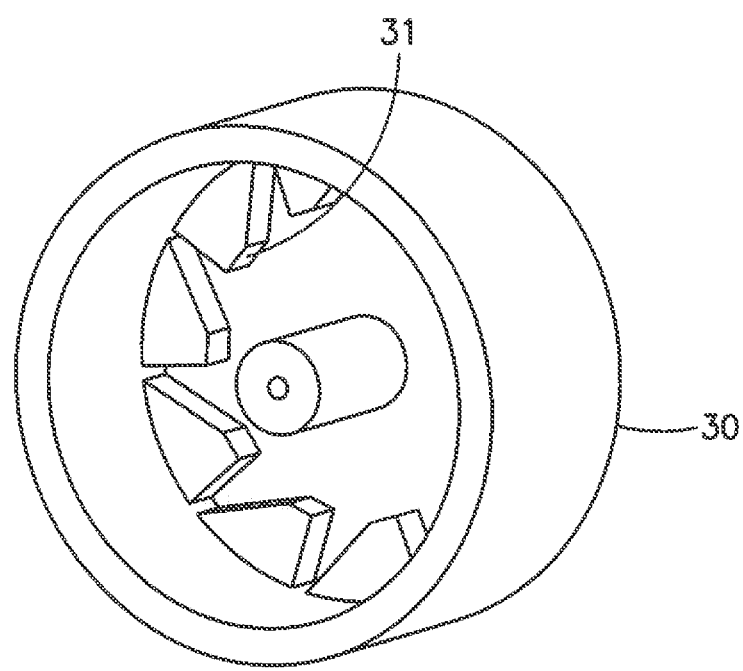
FIG. 16 is a perspective view of an alternative embodiment of the retainer plug.

As shown in FIG. 4, the internal threads 22 are formed in a first inner portion 45 of the hub body 16 toward the bottom proximal end 18 for coupling with the delivery pen 8. A second substantially cylindrical portion 42 is spaced axially from the internal threads 22 for receiving and supporting the retainer 30 as shown in FIG. 4. The retainer 30 has a substantially cylindrical side wall 44, a bottom end face 46, and a top face 48. In the embodiment shown, the side wall 44 is formed with threads 50 shown in FIGS. 5 and 6 for mating with complementing threads 52 of the hub body 16 shown in FIG. 10 for securing the retainer 30 in the hub body 16. The retainer 30 can also be secured in place by an adhesive or other attachment mechanism. In an alternative embodiment shown in FIG. 16, the retainer 30 can have a smooth outer surface on the side wall to fit within the hub body by a snap fit, friction fit, interference fit, adhesive, or other suitable method of securing the retainer in place. The retainer 30 is maintained in a fixed position with respect to the hub body 16 when installed to prevent rotation of the retainer 30 during use. The retainer 30 can be formed as two pieces bonded together or formed as a single one piece member. In the embodiment of FIG. 16, the retainer 30 has a flat end face and can include internal lugs 31 for engaging the end of the spring.

Figure 9:
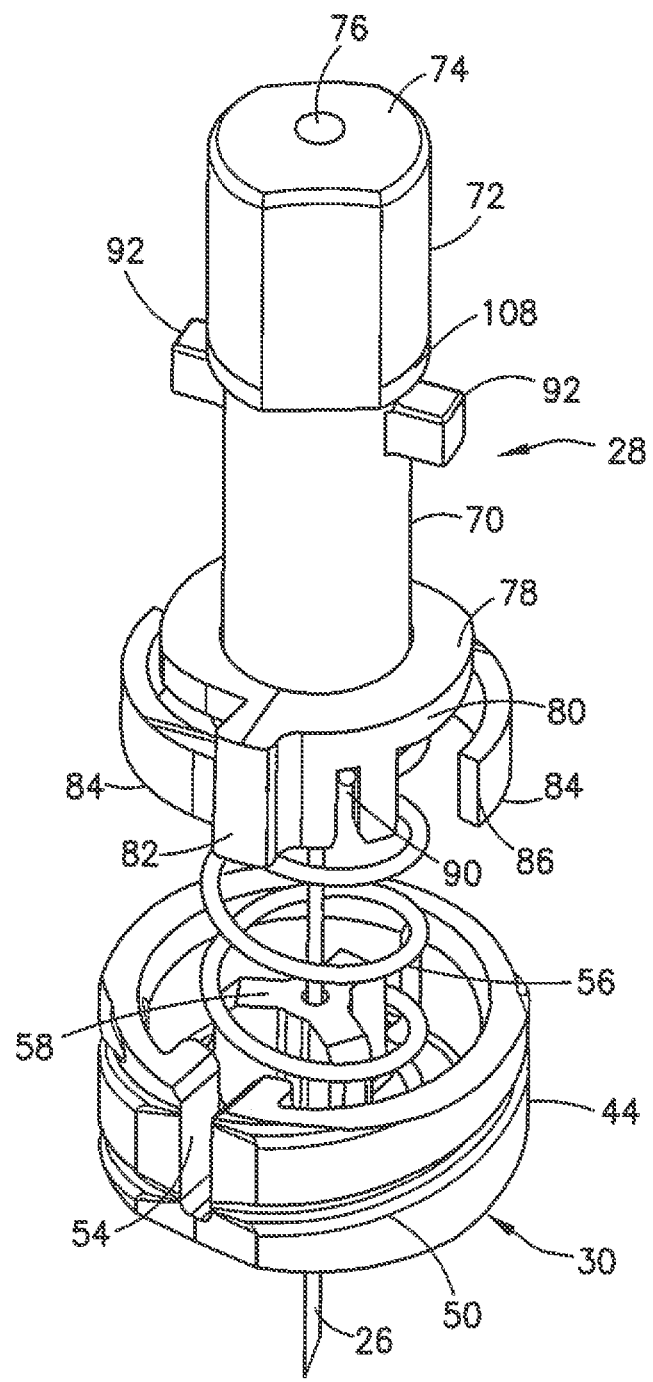
FIG. 9 is a top perspective view of the needle shield of FIG. 7.

As shown in FIG. 9, the side wall 44 of the retainer 30 includes a slot 54 forming a notch for receiving one end of the biasing member shown as the spring 56. The retainer 30 includes a center post 58 shown in FIG. 4 having an axial passage 64 forming an opening for receiving the needle 26. In the embodiment shown, the needle 26 is fixed in the axial opening 64 with a distal end projecting from the open end of the hub body 16 and a proximal end projecting into the bottom end of the hub body 16 for connecting to a reservoir in the delivery pen 8.

Referring to FIG. 9, the side wall 44 of the retainer 30 defines an open top end for receiving the spring 56. The axially extending post 58 projects in an upward axial direction for supporting and stabilizing the spring 56 and supporting the needle 26. In the embodiment shown, the spring 56 is a coil spring having a first bottom end with a leg 60 for mating with the slot 54 formed in the side wall 44 and to resist rotation of the spring 56 relative to the retainer 30. A second top end of the spring 56 includes a leg 62 for coupling to the needle shield 28 shown in FIG. 5. In other embodiments, the biasing member can have other configurations and shapes that are able to bias the needle shield 28 outward from the distal end of the hub body 16 and rotate the needle shield 28 relative to the hub body 16.

Figure 7:
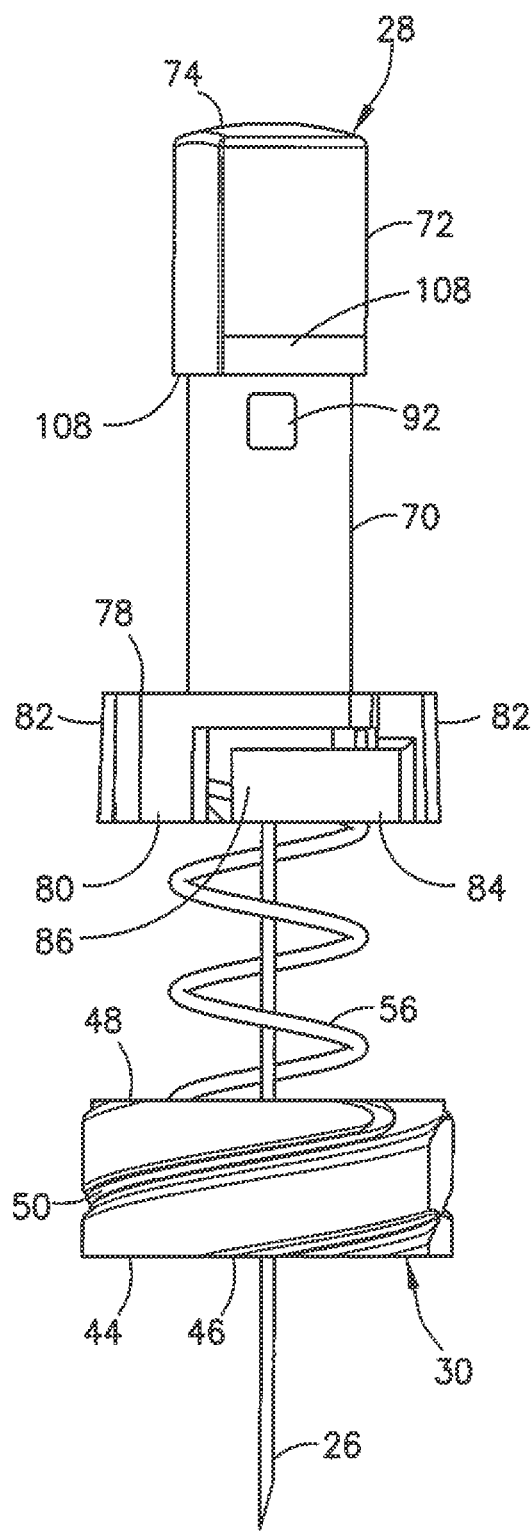
FIG. 7 is a side view of the needle shield.
Figure 8:
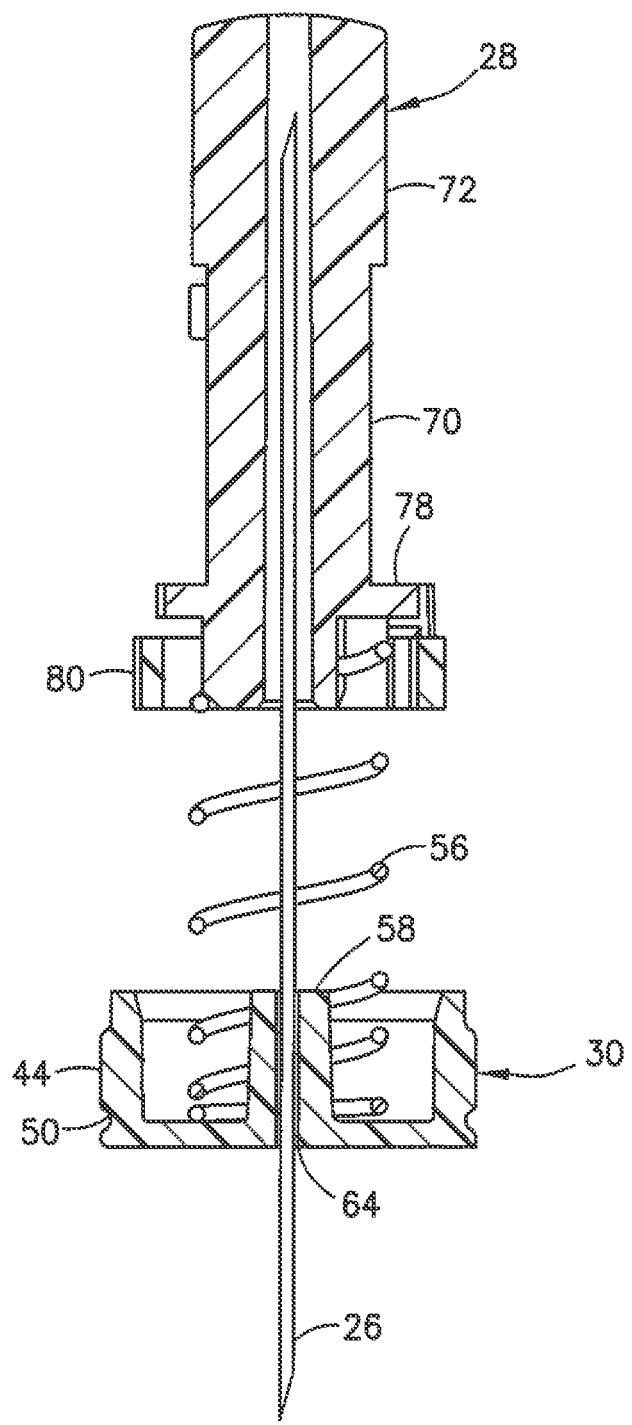
FIG. 8 is a cross sectional view of the needle shield of FIG. 7.

The needle shield 28 in the embodiment shown is configured to slide axially in the hub body 16 from an extended position shown in FIG. 4 to a retracted position shown in the sequential illustrations of FIGS. 14A-14E. The needle shield 28 has a body 70 with an end portion 72 extending axially from the body 70 as shown in FIGS. 7-9. The end portion 72 has a configuration to extend from and slide within the opening 24 in the open top end 20 of the hub body 16 during use. In the embodiment shown, the end portion 72 has flat side portions and rounded portions to slide within the hub body 16. As shown in FIG. 9, the axial face 74 of the end portion 72 has an opening and an axial passage 76 for sliding over the needle 26 during use.

An annular skirt 78 extends radially outward from the bottom proximal end of the body 70 of the shield 28 as shown in FIGS. 6-9. As shown in FIG. 7, the skirt 78 has a side wall 80 extending around the peripheral edge of the skirt 78. A lug 82 projects radially outward from the side wall 80 shown in FIGS. 6, 7 and 9 for mating with an inner surface of the hub body 16. In the embodiment shown in FIG. 11, two lugs 82 are formed on opposite sides of the side wall 80. The skirt 78 has a dimension with a top edge oriented for mating with an inwardly extending ledge 88 at the top distal end of the hub body 16 shown in FIG. 10 to retain the needle shield within the cavity of the hub body.

Figure 11:
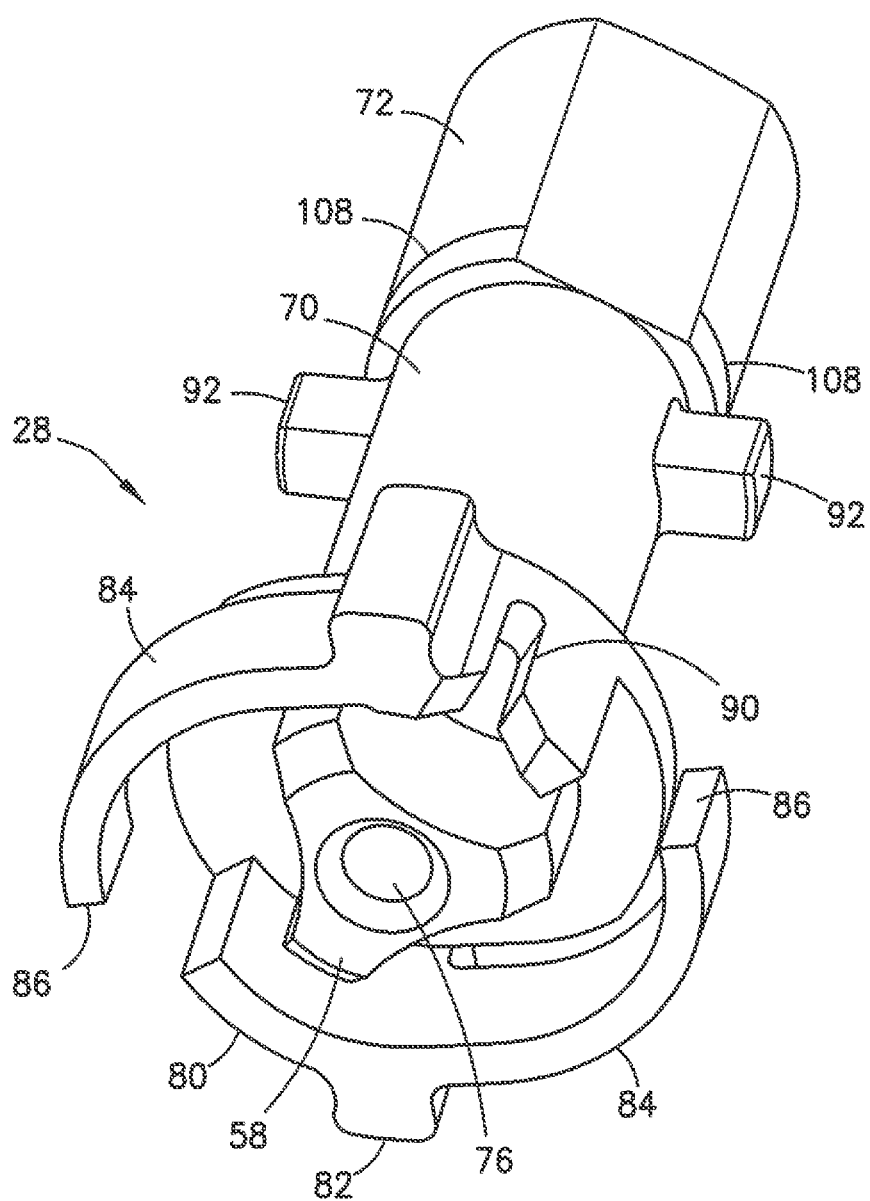
FIG. 11 is a bottom perspective view of the needle shield of the pen needle.
Figure 13:
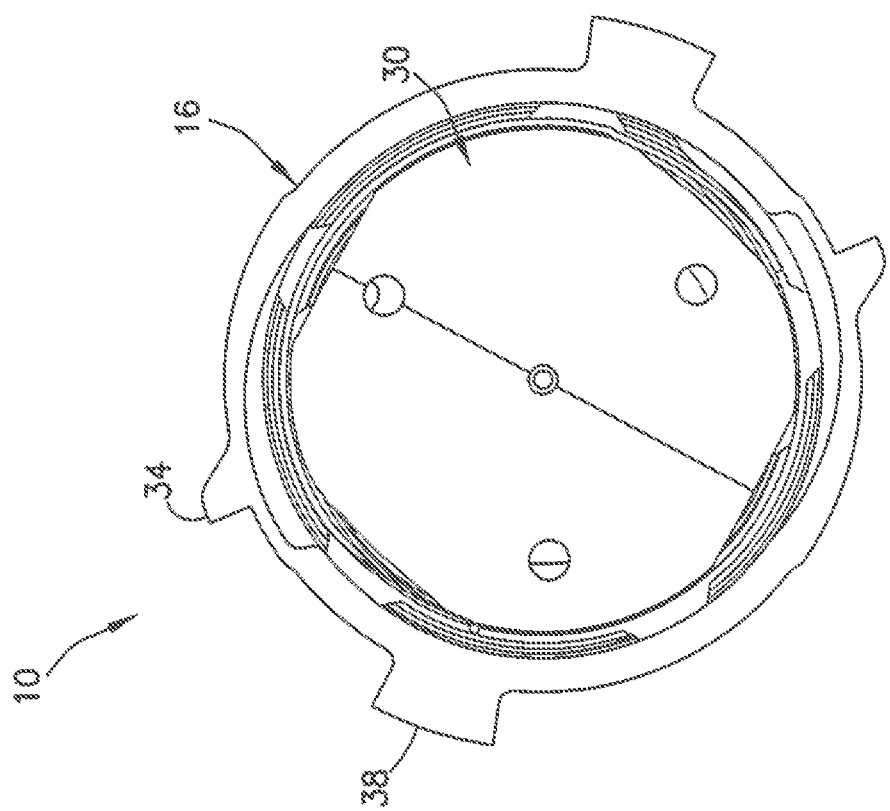
FIG. 13 is a bottom end view of the pen needle.
Figure 12:
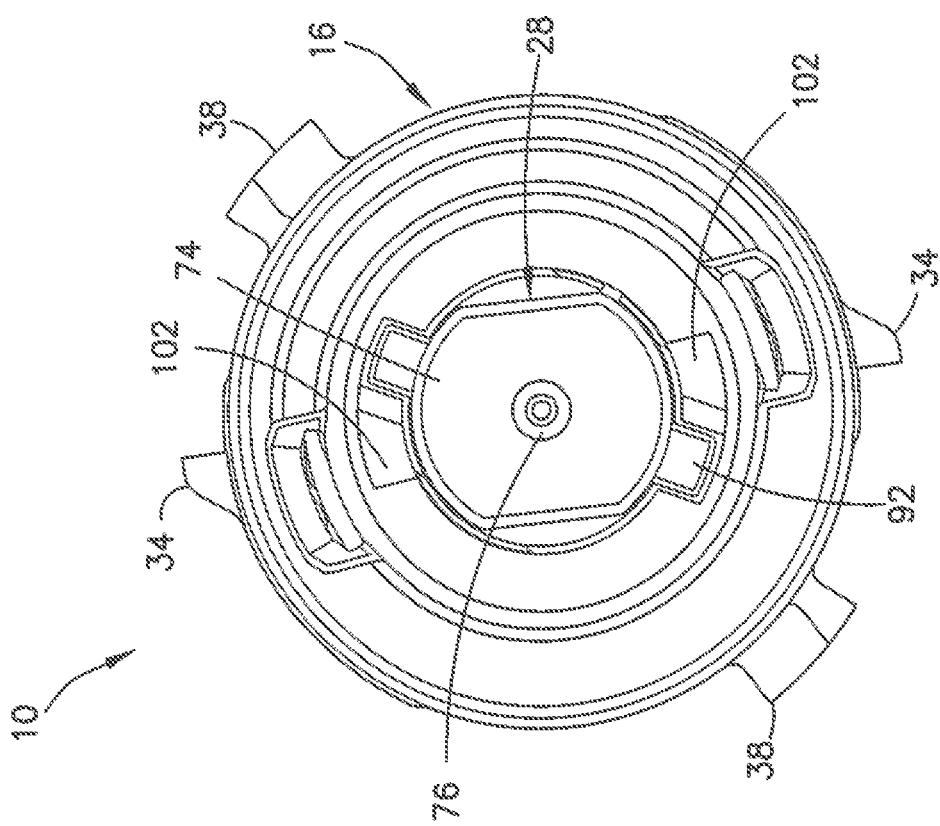
FIG. 12 is a top end view of the pen needle.

The side wall 80 of the skirt 78 is formed with a flexible member 84 as shown in FIG. 11 having a curvature complementing the curvature of the side wall 80. The flexible member 84 in the normal position is oriented to project outwardly from the side wall 80 toward the inner surface of the hub body. The flexible member 84 as shown in FIG. 9 and FIG. 11 has a substantially flat end face 86 for mating with an inner surface of the hub body 16.

Figure 14B:
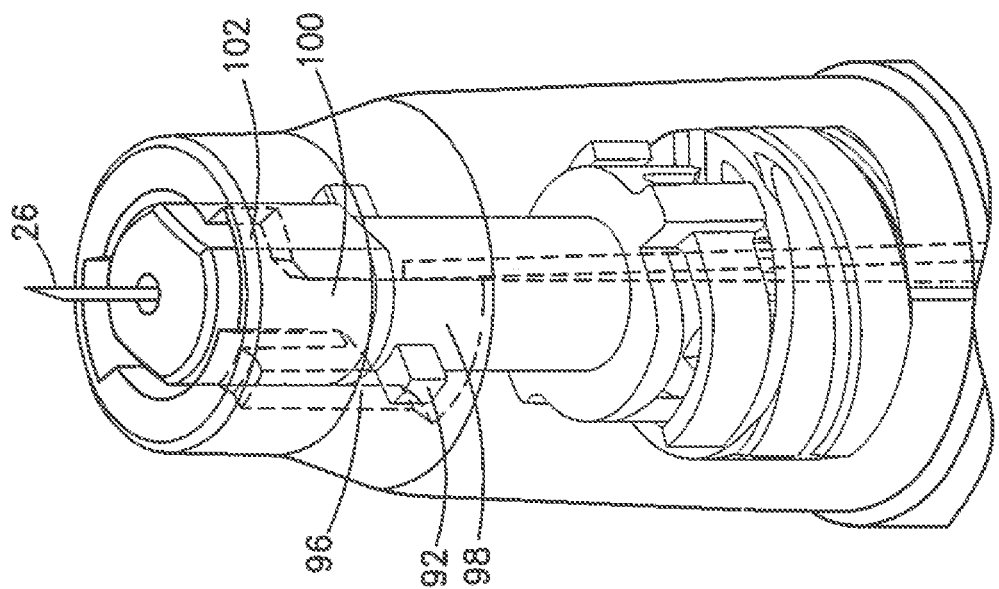
Figure 14A:
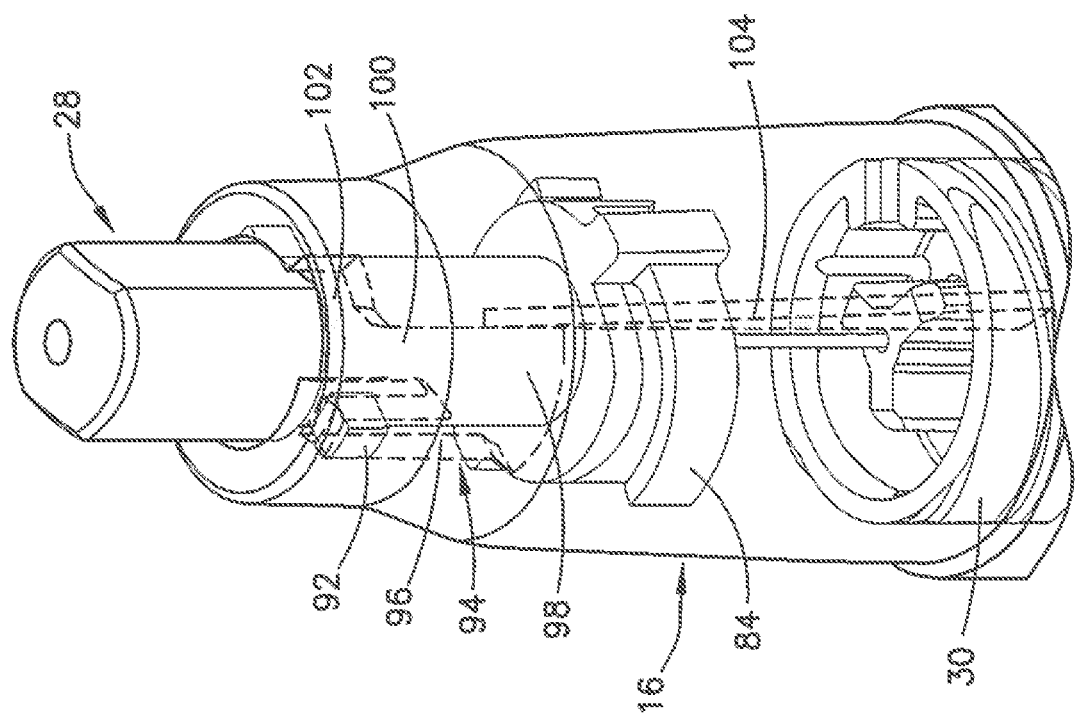
Figure 14D:
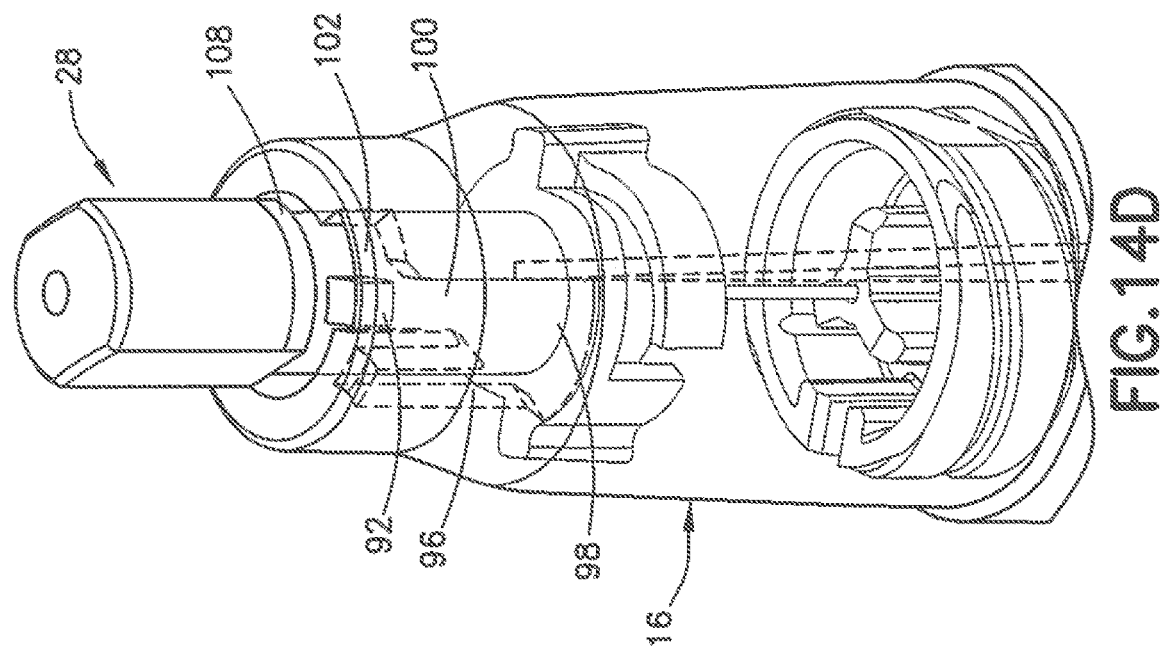
Figure 14C:
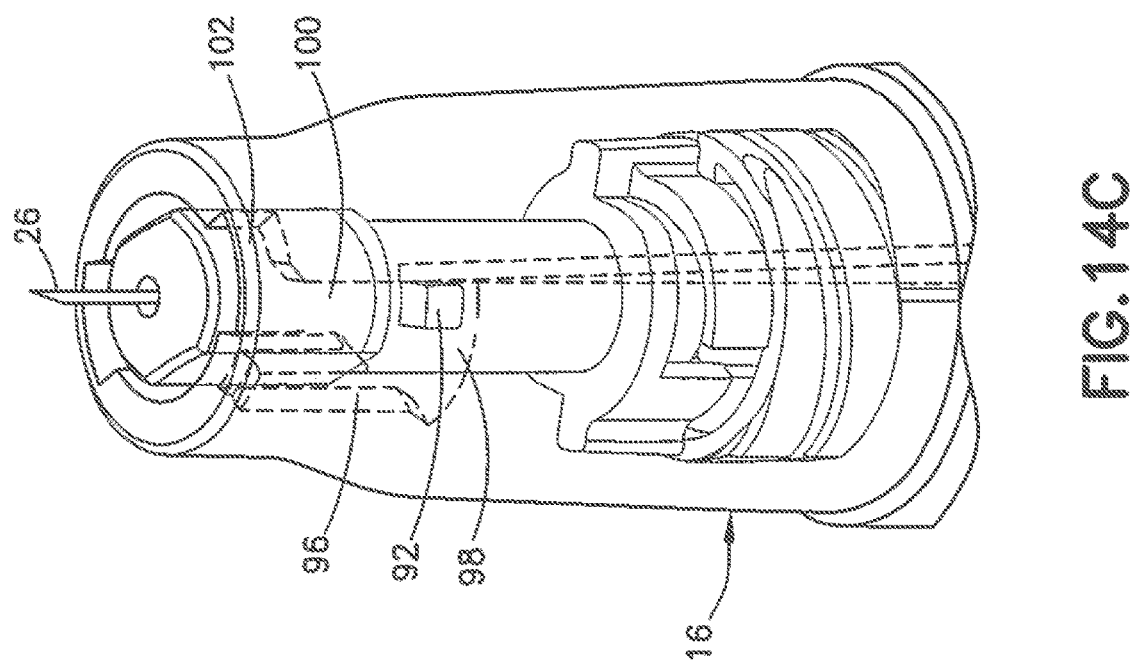

The needle shield 28 is configured for fitting within the axial cavity of the hub body 16 and sliding between an extended position shown in FIGS. 14A and 14D and a retracted position shown in FIGS. 14B and 14C through the opening in the top distal end of the hub body 16. The needle shield 28 is positioned in the hub body 16 through the bottom end of the hub body 16 followed by the spring 56 and the retainer 30. The retainer 30 is secured to the hub body 16 with the spring 56 and needle shield 28 captured within the hub body 16. The lugs 82 project outwardly from the skirt 78 and slide within the hub body 16 as shown in FIG. 4. In one embodiment, the lug 82 can slide in a longitudinally extending groove or recess 101 formed on the inner surface of the hub body 16 between ribs 104 shown in FIG. 4. The recess can have a length to allow the needle shield 28 to slide axially within the hub body 16 and a radial width to allow limited rotational movement of the needle shield 28 in the hub body 16.

As shown in FIG. 9, the spring 56 extends between the bottom face of the skirt 78 and the top face of the retainer 30. In one embodiment, the spring 56 is wound or twisted during assembly to provide a torsional or rotational force against the needle shield 28 for biasing and rotating the needle shield with respect to the hub body 16. The bottom end of the spring 56 is coupled to the retainer 30 to prevent rotation of the bottom end of the spring 56 relative to the retainer 30 and the hub body 16. The leg 62 at the top end of the spring 56 is coupled to the skirt 78 by a slot 90 that receives the leg 62 of the spring 56 so that the needle shield 28 is able to rotate relative to the retainer 30 and hub body 16.

The top end of the body 70 of the needle shield 28 includes at least one and typically two outwardly extending tabs 92 for mating with a track 94 formed on an inner surface at the top end of the hub body 16. The track 94 is configured for allowing the tabs 92 to slide axially within the track 94 so that the needle shield 28 can slide between the extended position where the end portion 72 of the needle shield 28 extends from the end of the hub body 16 to cover the needle 26 as shown in FIG. 4, and the retracted position shown in FIG. 14B. In the embodiment shown, a track 94 is provided for each of the tabs 92 to guide the tabs during the axial and rotational movement of the shield 28 with respect to the hub body 16. The track 94 in the embodiment shown is a recess or slot on an inner surface of the hub body 16 for guiding the tabs 92.

As best shown in FIGS. 14A-14E and 15, the track 94 is a slot that includes a first longitudinal section 96 extending in an axial direction and having a top end spaced from the top end of the hub body 16 so that the needle shield 28 can extend from the hub body 16 a distance where the needle shield 28 extends past the end of the needle 26. As shown in FIGS. 14A and 14B, the needle shield 28 can slide into the hub body 16 with the tabs 92 sliding in the first section 96 of the slot 94 to expose the needle 26 for injecting the patient.

The bottom end of the first longitudinal section 96 of the track 94 has a lateral section 98 with a dimension to receive the tab 92 and allow the tab 92 and needle shield 28 to rotate within the hub body 16. At the end of the lateral section 98 is a second longitudinal section 100 extending in the axial direction substantially parallel to the first longitudinal section 96. In the embodiment shown in FIG. 15, the wall portion between the first longitudinal section 96 and the second longitudinal section 100 terminates with inclined surfaces 103 to guide the tab 92 As shown in FIGS. 14A-14E, the second longitudinal section 100 has an axial length to extend axially toward the distal end of the hub body 16. In the embodiment shown, the longitudinal section 100 extends a distance greater than the axial length of the first section 96 and terminates at second lateral section 102 to enable the needle shield 28 to move distally from the hub body 16 a distance greater than when the tab 92 of the needle shield 28 travels in the first section 96. As shown, the second lateral section 102 has an inclined guide surface 105 and extends in a direction away from the second longitudinal section 100 in a direction opposite the first lateral section 98.

A longitudinally extending rib 104 is provided on the inner surface of the hub body 16 for cooperating with the flexible fingers 84 upon rotation of the needle shield with respect to the hub body 16 as the tabs 92 of the needle shield 28 slide through the lateral sections 98 and 102. The rib 104 is oriented to allow the flexible fingers 84 to slide over the rib 104 during use. The rib 104 forms a stop member to prevent the needle shield from being manually rotated back to the original position to prevent re-use of the device. The rib 104 also provides an audible and/or tactile feel to the user as the needle shield 28 rotates relative to the hub body 16. In other embodiments, the stop member is formed by a recess rather than a projecting rib.

In the initial position, the needle shield 28 is oriented in the position shown in FIG. 14A with the tab 92 received in the top end of the first section of the slot 94 with the needle shield 28 extending over the end of the needle 26. The hub body 16 is connected to the delivery pen where the proximal end of the needle 26 connects with the delivery pen for delivering the substance to the patient. The cover is used to connect the needle hub body 16 to the delivery pen by rotating the cover and the hub body to screw the hub body onto a threaded end of the delivery pen. In one embodiment shown in FIG. 4, the cover 14 includes an inwardly extending rib 106 that cooperates with the tab 34 and lug 38 forming a stop member.

As the cover is rotated and the hub assembly is screwed onto the delivery pen, the rib 106 slides over tab 34 when sufficient resistance is provided with the hub assembly properly tightened on the threaded end of the delivery pen forming an audible click or snap sound and/or a tactile feel that can be perceived by the user thereby indicating the hub assembly is properly tightened without over tightening. The rib 106 then rotates into the contact with lug 38 to provide sufficient resistance that can be perceived by the user after the audible click or resistance to provide an indication to the user that the hub assembly is correctly and properly coupled to the delivery pen.

The end of the hub assembly attached to the delivery pen is pressed against the skin of the patient so that the needle shield 28 retracts by sliding into the hub body 16 to expose the needle 26 where the needle 26 penetrates the skin of the patient as shown in FIG. 14B. In the position shown in FIG. 14B, the tab 92 slides along the first longitudinal section 96 of the track 94 to the bottom end where the first lateral section 98 is located. The spring 56 provides a torsional force to the needle shield 28 relative to the fixed retainer 30 and the hub body 16. The spring 56 rotates the needle shield 28 in the counter clockwise direction as shown in FIGS. 14A and 14B where the tab 92 slides along the first lateral section 98 toward the second longitudinal section 100 as shown in FIG. 14C. After the injection is completed, the hub body 16 and needle 26 are withdrawn from the patient. The spring 56 biases the needle shield 28 outwardly to the extended position as shown in FIG. 14D. The spring 56 is wound or twisted during assembly with the hub body 16 to provide the rotational force to needle shield 28 to move the tabs 92 through the lateral sections of the track.

The torsional force applied by the spring 56 rotates the needle shield 28 to the position shown in FIG. 14E where the tab 92 slides along the second lateral section 102. At the same time, the rotation of the needle shield 28 allows the flexible member 84 to slide over the rib 104 in the hub body 16 to the position shown in FIG. 14E where the end face 86 of the flexible member 84 contacts the side edge of the rib 104 and prevents the needle shield 28 from being rotated back toward a position where the tab 92 is aligned with the second longitudinal section 100 of the track 94, thereby preventing re-use of the hub assembly.

In one embodiment as shown, the top distal end of the first longitudinal section 96 is spaced a distance from the top end of the hub body 16 where the needle shield projects from the top end a first distance to cover the needle 26. The second lateral section 102 is shown as being open at the top end of the hub body 16 so that the needle shield 28 projects from the top end of the hub body a second distance that is greater than the first distance when the tab of the needle shield is received in the first longitudinal section 96. A visual indicator such as a colored band 108 is provided on an outer surface of the needle shield 28 and is positioned so that the indicator is not visible when the needle shield 28 is in the first extended position shown in FIG. 14A but is visible when the needle shield is in the second extended position shown in FIG. 14E thereby providing a visual indication to the user that the device has been used. The visual indicator 108 can be an annular recess, rib, colored ring or band or other feature that is able to provide a visual indication to the user that the device has be used and the needle shield is deployed to the extended locked position. The visual indicator 108 can be formed on the end portion 72 or the body portion 70.

In each of the foregoing embodiments, the components of the hub and outer cover are typically injection molded plastic, such as acrylonitrile butadiene styrene (ABS), polypropylene, or the like while the cannula is surgical grade stainless steel. Other materials and methods of manufacture known to those of ordinary skill in the art of medication pen technology may be adapted for use herein without departing from the scope of the invention. To assemble the parts, the hub assembly may be constructed with the needle separately, with adhesive applied in the interface area to secure the cannula to the hub, and this sub-assembly may then be assembled with an inner shield (optionally, depending on the embodiment), and fit by interference into an outer cover.

The foregoing description of the preferred embodiments is not to be deemed limiting of the invention, which is defined by the following claims. The foregoing description should provide the artisan of ordinary skill with sufficient information to practice variants of the embodiments described. Features and improvements described in dependent claims or in connection with one embodiment may be combined with those of another independent claim or another embodiment, provided they are not inconsistent therewith, without departing from the scope of the invention.

The invention claimed is:

1. A pen needle, comprising
a hub body having a proximal end for attachment to a delivery device, a distal end, and an inner surface having an axially extending track, said track having a lateral section at a distal end of said track;
a needle coupled to said hub body and having a distal end extending from said distal end of said hub body; and
a needle shield having a tab received in said track, said needle shield mounted in said hub body and slidable between a first extended position to cover said needle and a retracted position to expose said distal end of said needle, wherein said needle shield is rotatable in a first direction from a first angular position in which said needle shield slides in said hub body between said first extended position and said retracted position and a second angular position in which said needle shield slides to a second extended position, and rotates to a third angular position where said tab is received in said lateral section and said needle shield is locked in the second extended position; and
a locking mechanism actuated by rotation of said needle shield from said second angular position to said third angular position to lock said needle shield in said third angular position, said locking mechanism including a flexible finger biased radially outward from the needle shield, said flexible finger having a first end coupled to said needle shield and a second end, said hub body having an inwardly extending rib oriented between said track and said lateral section, said flexible finger configured for sliding over said rib of said hub body by rotation of said needle shield to said third angular position, whereby said second end of said flexible finger slides over said rib and engages said rib to prevent rotation of said needle shield and tab in a second direction.

2. The pen needle of claim 1, wherein
said tab slides within the track in said hub body to allow the needle shield to slide between the first extended position and the retracted position and to rotate from the first angular position to the second angular position.

3. The pen needle of claim 2, wherein
said track includes a first longitudinal section that allows said needle shield to slide from said first extended position to said retracted position and a second longitudinal section that allows said needle shield to slide from said retracted position to the second extended position, said second longitudinal section having an open distal end at an axial face of said distal end of said hub body, whereby said tab is visible through said open distal end.

4. The pen needle of claim 3, wherein
when said needle shield is in said second extended position said needle shield projects from said hub body a distance greater than when said needle shield is in said first extended position.

5. The pen needle of claim 4, wherein
said tab of said needle shield includes a visual indicator that is not visible when said needle shield is in said first extended position and is visible through said open distal end of said second longitudinal section when said needle shield is in said second extended position.

6. The pen needle of claim 5, wherein said flexible finger has a curved configuration and extends in a direction perpendicular to a longitudinal axis of said needle shield.

7. The pen needle of claim 3, wherein
the track includes a section extending between a bottom proximal end of said first longitudinal section and a bottom proximal end of said second longitudinal section to allow said tab to slide from said first longitudinal section to said second longitudinal section upon rotation of said needle shield relative to said hub body.

8. The pen needle of claim 7, wherein said lateral section at the distal end of said track is oriented for receiving the tab and preventing said needle shield from sliding from said second extended position to said retracted position by rotation of said needle shield relative to said hub body, wherein said lateral section is open to said axial face of said distal end of said hub body where said tab is visible when said tab is in said lateral section.

9. The pen needle of claim 3, wherein said needle shield includes a radially extending skirt at a proximal end, said skirt having a distal face configured for contacting an inwardly extending ledge on said hub body to limit axial movement of said needle shield in a distal direction.

10. The pen needle of claim 9, wherein said skirt includes a lug projecting radially outward, and said hub body includes a longitudinally extending channel for receiving said lug.

11. The pen needle of claim 1, further comprising a spring coupled to said hub body and said needle shield, said spring configured to bias said needle shield to said first extended position and to bias said needle shield to said second angular position.

12. The pen needle of claim 11, wherein
said spring comprises a coil spring having a first end fixed relative to said hub body and a second end fixed relative to said needle shield, and where said spring is configured to provide a torsional force to rotate said needle shield to the second angular position and a biasing force to bias said needle shield to the first extended position.

13. The pen needle of claim 1, wherein
said pen needle further comprises an outer cover received over the hub covering the needle and having at least one radially inward rib engaging at least one flexible tab on the hub body to provide a sensory indication for the user when the hub body is installed on the delivery device, and a stop member on the hub body to engage said rib to limit rotation of said cover relative to said hub body.

14. The pen needle according to claim 1, wherein said hub body has a circumferentially oriented flexible member located proximally of the distal end of the hub body, the end of said flexible member having a radially outward projection, and further comprising:
at least one stop member on the hub body projecting in a radially outward direction and a circumferential gap separating the flexible member from the stop member;
an outer cover received over the hub body covering the needle and having at least one radially inward projecting rib; wherein
engagement of the rib on the outer cover with the projection on the flexible tab causes the hub body to rotate with rotation of the outer cover; and
the projection on the flexible tab to slide over the rib on the outer cover when sufficient resistance to an applied rotational force of the outer cover with respect to the hub body for creating sensory feedback when the hub body is fully installed on the delivery device to prevent rotation of the outer cover with respect to the hub body when the hub body is seated on the medication pen.

15. A pen needle, comprising
a hub body having a proximal end for attachment to a delivery device and a distal end with an axial face;
a needle coupled to said hub body and having a distal end extending from said distal end of said hub body; and
a needle shield coupled to said hub body for sliding and rotating in said hub body, said needle shield having a radially extending tab that slides within a first track formed on an inner surface of said hub body for sliding said needle shield between a first extended position to cover said needle and a retracted position to expose said distal end of said needle, and sliding in a second track to a second extended position to cover the distal end of the needle, and wherein said needle shield and tab of said needle shield are rotatable from a first angular position in which said needle shield slides in said first track of said hub body from said first extended position to said retracted position and to a second angular position in which said needle shield slides in said second track to said second extended position where said needle shield is in a locked position in the second extended position, and where said tab is not visible when said tab is in said first track and is visible through said axial face of said hub body when in said second track and said needle shield is in said second extended position.

16. The pen needle of claim 15, wherein
said first track includes a first longitudinal section for sliding said needle shield from said first extended position to said retracted position, and said second track includes a second longitudinal section for sliding said needle shield from said retracted position to said second extended position.

17. The pen needle of claim 16, wherein
said track further comprises a first lateral section extending between said first longitudinal section and said second longitudinal section.

18. The pen needle of claim 15, wherein
said track further comprises a second lateral section having an open end at said axial face of said distal end of said hub body and said second longitudinal section allowing rotation of said needle shield from said second longitudinal section to said locked position, wherein said tab is visible in said second lateral section through said open end in said axial face of said hub body.

19. The pen needle of claim 18, further comprising
a spring coupled to said hub body and said needle shield to provide a biasing rotational force to said needle shield to rotate said needle shield from said first angular position to said second angular position, and where said spring provides an outwardly biasing force to slide said needle shield from said retraced position to said second extended position.

20. The pen needle of claim 15, further comprising
a spring coupled to said hub body and said needle shield, said spring configured to bias said needle shield to said first extended position and to bias said needle shield to said second angular position.

21. The pen needle of claim 15, wherein
said pen needle further comprises an outer cover received over the hub body covering the needle and having at least one radially inward rib engaging at least one flexible tab on the hub body to provide a sensory indication for the user when the hub body is installed on the delivery device, and a stop member on the hub body to engage said rib to limit rotation of said cover relative to said hub body.

22. The pen needle of claim 15, further comprising a locking mechanism including a flexible finger biased radially outward, said flexible finger having a first end coupled to said needle shield and a second end, said hub body having an inwardly extending rib, said flexible finger configured for sliding over said rib of said hub body by rotation of said needle shield to said second angular position, whereby said second end of said flexible finger slides over said rib and springs outward and contacts a side of said rib to prevent rotation of said needle shield and tab in a second direction.

23. The pen needle of claim 22, wherein said flexible finger has a curved configuration and extends in a direction perpendicular to a longitudinal axis of said needle shield.

24. The pen needle of claim 15, wherein said needle shield includes a radially extending skirt at a proximal end, said skirt having a distal face configured for contacting an inwardly extending ledge on said hub body to limit axial movement of said needle shield in a distal direction.

25. The pen needle of claim 24, wherein said skirt includes a lug projecting radially outward, and said hub body includes a longitudinally extending channel for receiving said lug.

26. A needle assembly, comprising
a hub body having a proximal end, a distal end, an inner surface having an axially extending track, and said track having an open area in a distal face of said hub body;
a needle coupled to said hub body and having a distal end extending from said distal end of said hub body; and
a needle shield mounted in said hub body for sliding between a first extended position to cover said needle, a retracted position to expose said needle, and locked second extended position, said needle shield having a tab configured for sliding in said hub body, and where said tab is not visible when said shield is in said first extended position and is visible through said open area in said distal face of said hub body when said needle shield is in said second extended position.

27. The needle assembly of claim 26, wherein said track in said hub body has a distal end with a lateral portion, said lateral portion having an open distal end forming the open area of said distal face of said hub body, and where said tab is visible through said open area in said distal face when said when said tab is in said lateral portion.

28. The needle assembly of claim 26, wherein said track includes a first longitudinal section receiving said tab to slide said needle shield from said first extended position to said retracted position, a second longitudinal section receiving said tab to slide said needle shield from said retracted position to said second extended position, said second section being open at a distal end to define said open area in said distal face of said hub body, whereby said tab is visible through said open area in said distal end of said hub body.

29. The needle assembly of claim 28, wherein said second longitudinal section of said track has a distal end with a lateral portion receiving said tab when said needle shield is rotated in said second extended position, said lateral portion being open at said distal end of said hub body to define said open area in said distal face of said hub body, and where said tab is visible through said open area when said tab is received in said lateral portion.

30. The needle assembly of claim 29, wherein said needle shield is rotatable in a first direction from a first angular position in which said needle shield slides in said hub body between said first extended position and said retracted position, and a second angular position in which said needle shield slides to said second extended position, and rotates to a third angular position where said tab is received in said lateral step portion, and said needle assembly further comprises a locking mechanism actuated by rotation of said needle shield from said second angular position to said third angular position to lock said needle shield in said third angular position.

* * * * *